United States Patent [19]

Morimoto et al.

[11] 4,139,545
[45] Feb. 13, 1979

[54] ARALKYL CARBOXYLIC ACID COMPOUNDS

[75] Inventors: Hiroshi Morimoto, Hyogo; Isuke Imada, Osaka; Masazumi Watanabe, Osaka; Mitsuru Kawada, Osaka, all of Japan

[73] Assignee: Takeda Chemical Industries, Ltd., Osaka, Japan

[21] Appl. No.: 573,158

[22] Filed: Apr. 30, 1975

[30] Foreign Application Priority Data

May 2, 1974 [JP] Japan .................................. 49-50003

[51] Int. Cl.$^2$ ...................... C07C 66/00; C07C 69/95
[52] U.S. Cl. ............................ 260/396 R; 560/144;
562/463; 568/763; 562/478; 562/465; 568/766;
562/470; 568/592; 568/648; 568/650; 568/651;
568/652; 260/399; 260/404; 260/405;
260/410.9 R; 260/413; 260/448 R; 260/501.1;
260/590 R; 424/305; 424/308; 424/309;
424/311; 424/316; 424/317; 424/318; 424/331;
424/341; 424/346; 560/53; 560/55; 560/60;
560/75; 560/105; 560/106; 560/109
[58] Field of Search .................................. 260/396 R

[56] References Cited

U.S. PATENT DOCUMENTS

3,728,363  4/1973  Morimoto et al. ............. 260/396 R

OTHER PUBLICATIONS

Chem. Abstracts, 33: 2896.
Chem. Abstracts, 73: 45055v.

*Primary Examiner*—Vivian Garner
*Attorney, Agent, or Firm*—Wenderoth, Lind & Ponack

[57] ABSTRACT

Novel compounds of the formulae

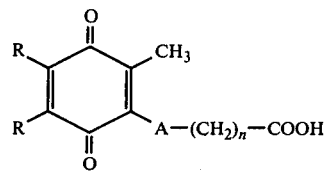

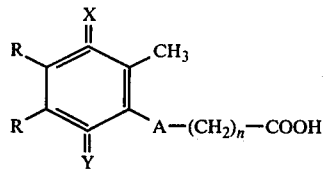

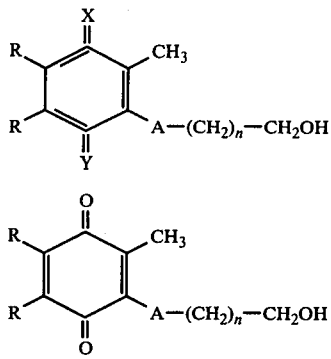

wherein R represents lower alkyl or lower alkoxy, A represents —$CH_2$—, —CO— or

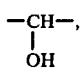

n represents an integer of 1 to 8, X represents hydrogen or hydroxyl which may be protected and Y represents hydroxyl which may be protected, and their esters show an excellent action on the lysosomal membranes of cells, and exhibit excellent pharmacological activities such as physiologic host defense control activity, especially immuno-potentiating activity.

21 Claims, No Drawings

ARALKYL CARBOXYLIC ACID COMPOUNDS

This invention relates to novel compounds of any of the formulae (I) to (IV)

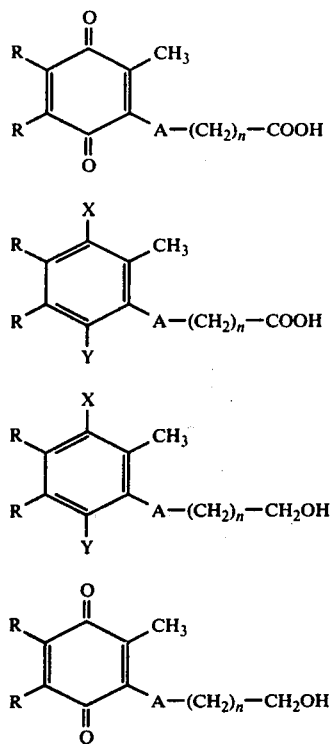

wherein R represents lower alkyl or lower alkoxy, A represents —CH$_2$—, —CO— or

n represents an integer of 1 to 8, X represents hydrogen or hydroxyl which may be protected and Y represents hydroxyl which may be protected, and their esters.

The present inventors have succeeded in synthesizing the novel compounds of any of the formulae (I) to (IV) and found (1) that any of the compounds (I) to (IV) have an excellent action on lysosomal membranes of cells, and physiologic host defense control activity, especially immuno-potentiating activity, and that accordingly these compounds are of use as medicaments for human or animal therapy; (2) that these compounds are invariably simple in chemical structure and suitable for industrial production; (3) that these compounds have an adequate degree of hydrophilicity and lend themselves conveniently to formulation into pharmaceutical products; and (4) that these compounds are comparatively stable against acid and light and can be employed advantageously as medicaments.

The present invention has been accomplished on the basis of these findings.

Thus, the principal object of this invention is to provide the novel compounds of any of the formulae (I) to (IV) and their esters useful as medicines such as physiologic host defense control agents. Another object of this invention is to provide an industrially feasible method for the production of these novel compounds, and a further object is to provide pharmaceutical compositions comprising one or more of these compounds.

In any of the formulae (I) to (IV), the lower alkyl represented by R is advantageously one having 1 to 4 carbon atoms, and is exemplified by methyl, ethyl, n-propyl, i-propyl, n-butyl and i-butyl.

The lower alkoxy represented by R is advantageously one having 1 to 4 carbon atoms, and is exemplified by methoxy, ethoxy, n-propoxy, i-propoxy, n-butoxy and i-butoxy. The integer represented by n is advantageously 4 or 5 when R is lower alkyl, while the integer is advantageously 1, 2, 7 or 8 when R is lower alkoxy.

As to the formulae (II) and (III), the protective group for the hydroxyl X or Y may be any type of groups which can be easily removed and is exemplified by alkyl, aralkyl, acyl, acetal and silyl.

The alkyl of the protective group is advantageously one having up to 4 carbon atoms and exemplified by methyl, ethyl, n-propyl, i-propyl, n-butyl and i-butyl. The aralkyl for the protective group is advantageously benzyl.

As the acyl for the protective group, there may be mentioned alkyl carbonyl, aryl carbonyl, aralkyl carbonyl, especially alkyl carbonyl having 1 to 4 carbon atoms such as acetyl, n-propionyl and n-butyryl. The acetal for the protective group is advantageously α-tetrahydropyranyl or methoxymethyl.

As the silyl for the protective group, trimethylsilyl is used advantageously.

Referring to the formulae (I) and (II), the type of ester is advantageously alkyl ester, aryl ester or aralkyl ester, the alkyl, aryl and aralkyl moieties of which may be substituted.

The alkyl moiety of the alkyl ester is advantageously one having up to 4 carbon atoms and exemplified by methyl, ethyl, n-propyl, i-propyl, n-butyl and i-butyl. The aryl moiety of the aryl ester is advantageously one having up to 7 carbon atoms and exemplified by phenyl and p-tolyl. The aralkyl moiety of the aralkyl ester is advantageously one having up to 8 carbon atoms and exemplified by benzyl and phenethyl.

The substituent of these moieties may be sulfo, carboxyl, formyl, hydroxyl or/and amino.

Referring to the formulae (III) and (IV), the type of ester is advantageously alkyl carboxylic acid ester, aryl carboxylic acid ester or aralkyl carboxylic acid ester, the alkyl, aryl and aralkyl moieties of which may be substituted.

As the alkyl, aryl and aralkyl moieties and the substituents of these moieties, those mentioned above in connection with the esters of the compounds (I) and (II) may be mentioned.

The compounds of the formulae (I) to (IV) may be produced by, for example, the processes schematically shown and explained in detail below:

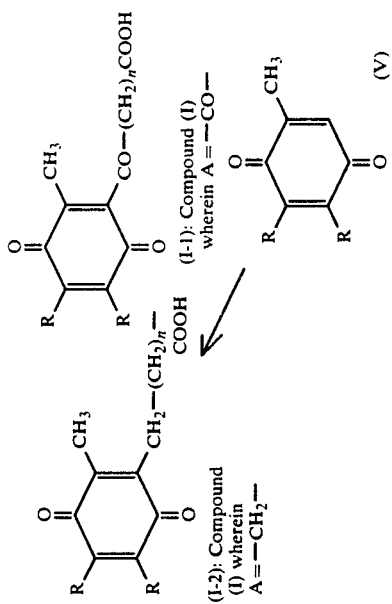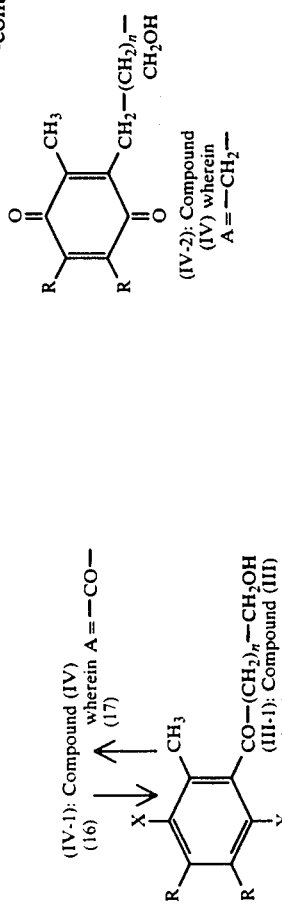
wherein R, n, X and Y have the same meaning as defined above.

The group of compounds (I), (II), (III) and (IV) may all be synthesized starting from the compound (VII),

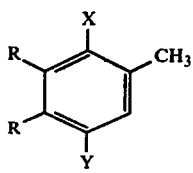

wherein R, X and Y have the same meaning as defined above, which is a known compound, and some of the compounds included in this group may be synthesized starting from a compound (V)

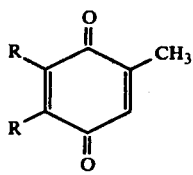

wherein R has the same meaning as defined above, which is also a known compound.

Namely, when the compound (VII) is employed for the starting compound, it is first converted into the compound (II-1)

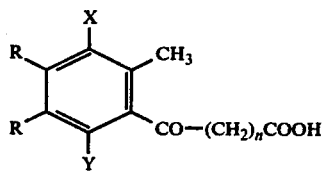

wherein R, n, X and Y have the same meaning as defined above, which is one of the object compounds, and then the latter may further be converted into other compounds through various synthetic means. On the other hand, when the compound (V) is selected as the starting material, one may directly synthesize the compound (I-2)

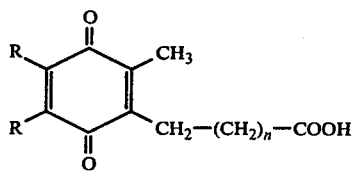

wherein R and n have the same meaning as defined above, which is one of the objective compounds, and then the latter may be changed into the compound (II-2).

The processes for producing the compounds (I), (II), (III) and (IV), namely the steps (1) to (18), will be more particularly mentioned below:

Step (1)

In the step (1), a compound (VII) is reacted with a compound of the formula (VIII)

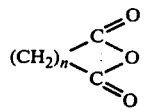  (VIII)

wherein n has the same meaning as defined above, or a compound of the formula (IX)

$$Z-(CH_2)_n\underset{\underset{O}{\|}}{C}-Hal \qquad (IX)$$

wherein Z represents carboxyl which may be esterified, Hal represents halogen atom and n has the same meaning as defined above, to obtain the compounds (II-1). In this reaction it is advantageous to employ a catalyst.

As the catalyst, any catalysts employed in the Friedel-Crafts Reaction, for example, sulfonic acid, phosphoric acid, poly phosphoric acid, and Lewis acids such as aluminum chloride are employed. While this reaction advances in the absence of a solvent, it is usually conducted in the presence of an inert solvent such as nitrobenzene, carbon disulfide, or tetrachloroethane. The reaction temperature is advantageously about 50° C.–150° C.

Step (2)

In the step (2), a compound (II-1) is oxidized to obtain the compounds (I-1).

This oxidation is performed by a procedure which is conventional. Any oxidation procedure by which phenol may be converted to quinone can be employed with advantage. The preferred oxidizing agents are ferric chloride, silver oxide, manganese dioxide, hydrogen peroxide, peracetic acid, performic acid, perbenzoic acid, potassium permanganate, potassium nitrosodisulfonate, and potassium dichromate.

This oxidation is generally conducted in a suitable solvent. Any solvent that does not intefere with this oxidation may be employed for this purpose; thus, for example, water, a dilute aqueous solution of an acid or an alkali, acetone, ethanol, dioxane, ether, acetic acid and so on may be mentioned. The progress of the reaction may be monitored by thin-layer chromatography. For such detection purpose, a yellow spot, a positive reaction to leucomethylene blue or ultraviolet absorption spectrometry may be employed.

While the reaction temperature and time are dependent to a certain extent upon the type of oxidizing agent, generally preferred conditions are about 0° C. to 25° C. and about 0.5 to 5 hours. Satisfactory results are also obtained when the reaction is conducted in a suitable buffer solution (e.g. phosphate buffer).

Step (3)

In the step (3), a compound (II-1) is reduced to obtain the compound (II-2).

The procedure for this reduction may be any procedure by which the carbonyl of the compounds (II-1) may be converted to a methylene. As such procedures, there may be mentioned Clemmensen reduction, Wolff-Kishner reduction, a method comprising converting the starting compound to the dithioacetate and reducing the latter through desulfuration, and catalytic reduction. Generally, this reaction is advantageously conducted in the presence of a suitable solvent. The solvent may be any solvent that does not interfere with the reaction, being exemplified by ether, methanol, ethanol, benzene, toluene, xylene, ethylene glycol, triethylene glycol, acetic acid and so on. The aforementioned reduction reactions may each be easily carried out in the routine manner.

Step (4)

In the step (4), a compound (II-2) is oxidized to obtain the compounds (I-2). This oxidation is performed by the same means as those set forth in the step (2).

Step (5)

In the step (5), a compound (II-1) is reduced to obtain the compounds (II-3).

The procedure for this reduction may be any procedure by which ketone may be converted to alcoholic hydroxyl without effecting the carboxyl, thus being exemplified by catalytic reduction, reduction by means of reducing agents such as sodium borohydride.

Step (6)

In the step (6), a compound (II-3) is oxidized to obtain the compounds (I-3).

The procedure for this oxidation may be any procedure by which phenol may be converted to quinone without affecting the alcoholic hydroxyl. The oxidizing agent is advantageously ferric chloride, silver oxide or potassium nitrosodisulfonate.

This oxidation is performed under conditions similar to those set forth in the step (2).

Step (7)

In the step (7), a compound (I-1) is reduced to obtain the compounds (II-2).

As for the procedures of reduction, those mentioned hereinbefore in connection with the step (3) may be employed. In this step, the compounds (II-2) wherein X and Y are hydroxyl are obtained.

Step (8)

In the step (8), a compound (I-1) is reduced to obtain the compounds (II-1). This reduction may be accomplished by any procedure by which quinone can be converted to hydroquinone without affecting the carbonyl. Thus, for example, reduction by means of a hydrosulfite may be employed with advantage. In this step, the compounds (II-1) wherein X and Y are hydroxyl are obtained.

Step (9)

In the step (9), a compound (V) is reacted with a peroxide of a carboxylic acid of the formula (IX)

$$Z-(CH_2)_{n+1}-COOH \quad (VI)$$

wherein n and Z have the same meaning as defined above or of its anhydride.

The aforementioned peroxide of the carboxylic acid (VI) or of an anhydride thereof may be any compound that, when heated, gives rise to an alkyl radical with the evolution of carbon dioxide, and can be obtained by permitting a peroxide (e.g. hydrogen peroxide, a metal salt thereof, lead tetraacetate, etc.) to act upon the carboxylic acid or an acid halide or acid anhydride thereof.

The reaction of this step is advantageously conducted in a suitable inert solvent such as, n-hexane, ligroine, toluene, xylene, acetic acid or propionic acid. The reaction temperature is advantageously in the range of about 80° C. to 100° C., and the reaction time is desirably in the range of about 0.5 to 3 hours. This reaction proceeds with the evolution of carbon dioxide under very mild conditions, accompanied only by a minimum of side reaction, enabling the desired product to be produced in satisfactory yield and, after the reaction, the unreacted starting material to be completely recovered.

The present reaction may also be conducted under conditions such that the aforesaid peroxide is produced in the reaction system. For example, the compound (V) may be reacted with a carboxylic acid of formula (VI) or its anhydride in the presence of a tetravalent lead compound (e.g. lead tetraacetate). This reaction is advantageously carried out in a suitable inert solvent (e.g. n-hexane, ligroine, toluene, xylene, acetic acid, propionic acid, etc.), the reaction temperature being desirably maintained in the range of 50° C. to 150° C.

Step (10)

In the step (10), a compound (I-2) is reduced to obtain the compounds (II-2). The reduction procedure may be any procedure by which quinone may be converted to hydroquinone, thus being exemplified by catalytic reduction, reduction by means of a hydrosulfite, etc., which may be employed with advantage. In this step the compounds (II-2), wherein X and Y are hydroxyl are obtained.

Step (11)

In the step (11), a compound (II-1) is reduced to obtain the compounds (III-3). The procedure for this reduction may be any procedure by which carboxyl may be converted to an alcoholic hydroxyl. As such procedures, there may be mentioned reduction by means of lithium aluminum hydride. Generally this reduction is advantageously conducted in the presence of a suitable solvent. The solvent may be any solvent that does not intefere with the reduction being exemplified by ethers (e.g. diethyl ether, tetrahydrofuran, dioxane).

Step (12)

In the step (12), a compound (III-3) is reduced to obtain the compounds (III-2). The procedure for this reduction may be any procedure by which alcoholic hydroxyl may be converted to hydrogen. The reduction may be carried out by per se known reduction means. Thus catalytic reduction may be employed with advantage. As the catalyst, palladium, platinum oxide or the like may be advantageously employed. Generally, this reduction is advantageously conducted in the presence of a suitable solvent. The solvent may be any solvent that does not interfere with the reduction, being exemplified by acetic acid and alcohols (e.g. methanol, ethanol). This reduction may be advantageously conducted in the presence of for example, an acid (e.g. hydrochloric acid, perchloric acid etc.).

Step (13)

In the step (13), a compound (III-2) is oxidized to obtain the compounds (IV-2). The procedure for this oxidation may be any procedure by which phenol may be converted to quinone without affecting the hydroxyl. The oxidizing agent is advantageously ferric chloride, silver oxide, nitrosodisulfonate and so on.

This oxidation is generally conducted in a suitable solvent. Any solvent that does not intefere with this oxidation may be employed for this purpose; thus, for example, water, a dilute aqueous solution of an acid or an alkali, acetone, ethanol, dioxane, ether, acetic acid dimethylformamide and so on may be mentioned.

While the reaction temperature and time are dependent to a certain extent upon the type of oxidizing agent, generally preferred conditions are about 0° C. to 25° C. and about 0.5 to 5 hours.

Step (14)

In the step (14), a compound (III-3) is oxidized to obtain the compounds (IV-3). This oxidation is performed by procedures similar to those set forth in the step (13).

Step (15)

In the step (15), a compound (IV-3) is oxidized to obtain the compounds (IV-1). This oxidation is advantageously conducted after protecting the —CH$_2$OH group in a compound (IV-3). The protective group may be any type of group which can be easily removed and is exemplified by acyl (e.g. acetyl, benzyl, benzoyl, etc.), acetal (tetrahydropyranyl etc.). The preferred oxidizing agents are manganese dioxide and chromium trioxide.

Step (16)

In the step (16), a compound (IV-1) is reduced to obtain the compounds (III-1). This reduction is performed by procedures similar to those set forth in the step (8). In this step, the compounds (III-1) wherein X and Y are hydroxyl are obtained.

Step (17)

In the step (17), a compound (III-1) is oxidized to obtain the compounds (IV-1). This oxidation is performed by procedures similar to those set forth in step (13).

When the compounds (I) and (II) thus obtained have free carboxyl, these compounds can be esterified by a procedure known per se to the compounds (I) and (II) having esterified carboxyl.

Step (18)

In the step (18), a compound (I-2) is reduced to obtain the compounds (III-2). This reduction is performed by procedures similar to those set forth in the step (11).

To accomplish the aforementioned esterification, there may for instance be employed the technique which comprises reacting a compound (I), (II) or a reactive derivative thereof at their carboxyl function with an alcohol, phenol compound, alkyl halide, aralkyl halide or dialkyl sulfate or diazomethane, for instance. As the reactive derivatives of carboxylic acids, there may be mentioned the carboxylic anhydrides, carboxylic halides, metal carboxylate (e.g. sodium, potassium, silver and other salts of carboxylic acids) and so on. The alcohol may for example be methanol, ethanol, n-propanol, isopropanol, n-butanol, isobutanol, etc.; the alkyl halides are methyl iodide, ethyl iodide, benzyl chloride and so on.

Among the compounds (I) and (II), the compounds (I-3) and (II-3) can be esterified also at their

by procedures similar to those mentioned hereinafter in connection with the esterification of the compounds (III) and (IV).

When the compounds (I) and (II) thus obtained have esterified carboxyl, these compounds can be converted to the compounds (I) and (II) having free carboxyl by a hydrolytic procedure which is known per se.

The above hydrolysis is conducted with advantage in the presence of, for example, a mineral acid (e.g. sulfuric acid, hydrochloric acid) or an alkaline substance (e.g. sodium hydroxide, potassium hydroxide, calcium hydroxide).

Further, the hydrolysis reaction is conducted with advantage in the presence of suitable antioxidant (e.g. pyrogallol etc.) or reducing agent (e.g. hydrosulfite, etc.).

Among the compounds (I) and (II), the compound (I-3) and (II-3), having esterified alcoholic hydroxyl can be coverted to the compound (I-3) and (II-3) having hydroxyl by procedures similar to those mentioned hereinbefore.

When the compounds (III) and (IV) thus obtained have alcoholic hydroxyl, the compounds can be esterified by a procedure known per se to the compounds (III) and (IV) having esterified alcoholic hydroxyl.

To accomplish the esterification, there may for instance be employed the method which comprises reacting the compound (III) or (IV) having alcoholic hydroxyl with carboxylic acid compound or a reactive derivative thereof. As the carboxylic acid there may be mentioned the alkyl carboxylic acid, aryl carboxylic acid, aralkyl carboxylic acid. As the reactive derivatives of the carboxylic acids, there may be mentioned the carboxylic anhydrides, carboxylic halides, carboxylic acid lower alcohol esters, metal carboxylate and so on.

In the case of the compounds (III-3) and (IV-3), generally this esterification would occur at the —CH$_2$OH and

groups, but it is possible to esterify at the —CH$_2$OH group alone by the selection of conditions, such as that the ratio of the compounds (III-3) or (IV-3) to the carboxylic acid or its reactive derivative is adjusted 1 to 1.

When the compounds (III) and (IV) thus obtained have esterified alcoholic hydroxyl, the compounds can be converted to the compound (III) and (IV) having alcoholic hydroxyl by a hydrolytic procedure which is similar to those set forth in connection with the compounds (I).

Thus obtained compounds (I) to (IV) can be easily isolated by procedures known per se, such as pH adjustment, phasic transfer, concentration, distillation under reduced pressure, chromatography, crystallization, recrystallization and the like.

In the case of the compounds (I) and (II) having free carboxyl, these compound may be isolated either as the free carboxylic acid or in the form of a pharmaceutically acceptable salt.

These free carboxylic acids may, after being isolated, be converted to a pharmaceutically acceptable salt. The pharmaceutically acceptable salt mentioned above is exemplified by metal salts such as alkali metal salts, e.g. sodium and potassium salt, alkaline earth metal salts, Infrared absorption spectrum $\nu_{max}^{KBr}$ cm$^{-1}$: 3400(OH), 1700(COOH).

Nuclear magnetic resonance spectrum ($\tau$ in deuterochloroform): 8.8–8.0(CH$_2$, multiplet), 7.9–7.2(CH$_2$, multiplet), 7.90(ring CH$_3$, singlet), 7.80(ring CH$_3$, singlet), 3.41(ring proton, singlet).

Elemental analysis, C$_{15}$H$_{22}$O$_3$— Calculated: C, 71.97; H, 8.86. Found: C, 71.67; H, 9.02.

EXAMPLE 8

6-(2'-Hydroxy-3',4',6'-trimethylbenzoyl)hexanoic acid (formula II-1 wherein R=H$_3$C, X=H, Y=OH, n=5, in the free form) (0.326 part) was reduced by a procedure similar to that described in Example 7. The procedure provided 7-(2'-hydroxy-3',4',6'-trimethylphenyl)heptanoic acid (formula II-2 wherein R=H$_3$C, X=H, Y=OH, n=5, in the free form) (0.25 part) as colorless needles melting at 91°–104° C.

Infrared absorption spectrum $\nu_{max}^{KBr}$ cm$^{-1}$: 3450(OH), 1710(COOH).

Nuclear magnetic resonance spectrum ($\tau$ in deuterochloroform): 8.9–8.1(CH$_2$, multiplet), 8.0–7.2(CH$_2$, multiplet), 7.87(ring CH$_3$, singlet), 7.78(ring CH$_3$, singlet), 3.42(ring proton, singlet).

Elemental analysis, C$_{16}$H$_{24}$O$_3$— Calculated: C, 72.69; H, 9.15. Found: C, 72.48; H, 9.08.

EXAMPLE 9

9-(2'-Hydroxy-3',4',6'-trimethylbenzoyl)nonanoic acid (formula II-1 wherein R=H$_3$C, X=H, Y=OH, n=8, in the free form) (1.1 part) was reduced and treated by a procedure similar to that described in Example 7. The procedure provided 10-(2'-hydroxy-3',4',6'-trimethylphenyl)decanoic acid (formula II-2 wherein R=H$_3$C, X=H, Y=OH, n=8, in the free form) (0.4 part) as a colorless oil.

EXAMPLE 10

9-(2'-Hydroxy-3',4'-dimethoxy-6'-methylbenzoyl)nonanoic acid (formula II-1, wherein R=H$_3$CO, X=H, Y=OH, n=8, in the free form) (0.254 part), zinc amalgam (0.56 part), toluene (1 volume part), 35% hydrochloric acid (0.5 volume part) and a small proportion of water were refluxed for 5 hours. The toluene layer was separated and the water layer was extracted with diethyl ether. The toluene layer was combined with the ethereal layer, washed with water and dried. The solvents were then distilled off under reduced pressure and the residue was recrystallized from ligroine. The foregoing procedure provided 10-(2'-hydroxy-3',4'-dimethoxy-6'-methylphenyl)decanoic acid (formula II-2 wherein R=H$_3$CO, X=H, n=8, in the free form) (0.14 part) as colorless powdery crystals melting at 62.5°–66° C.

Nuclear magnetic resonance spectrum ($\tau$ in deuterochloroform): 8.80–8.13(CH$_2$, multiplet), 7.78(ring CH$_3$, singlet), 7.57(COCH$_2$, CH$_2$CO, triplet), 6.20(OCH$_3$, singlet), 6.16(OCH$_3$, singlet), 4.77(ring proton, singlet).

Elemental analysis, C$_{19}$H$_{30}$O$_5$— Calculated: C, 67.43; H, 8.94. Found: C, 67.50; H, 8.89.

EXAMPLE 11

5-(2'-Hydroxy-3',4'-dimethoxy-6'-methylbenzoyl)pentanoic acid (formula II-1 wherein R=H$_3$CO, X=H, Y=OH, n=4, in the free form) (1.49 part) was reduced and treated by a procedure similar to that described in Example 10. The procedure provided 6-(2'-hydroxy-3',4'-dimethoxy-6'-methylphenyl)hexanoic acid (formula II-2 wherein R=H$_3$CO, X=H, Y=OH, n=4, in the free form) (0.6 part) as colorless crystals melting at 38°–44° C.

Elemental analysis, C$_{15}$H$_{22}$O$_5$— Calculated: C, 63.81; H, 7.85. Found: C, 63.54; H, 7.70.

EXAMPLE 12

A mixture of 3-(2'-hydroxy-3',4'-dimethoxy-6'-methylbenzoyl)propionic acid (formula II-1 wherein R=H$_3$CO, X=H, Y=OH, n=2 in the free form) (0.536 part), zinc amalgam (1 part), concentrated hydrochloric acid (1 volume part), water (2 volume parts) and toluene (2 volume parts) was refluxed for 5 hours and, after cooling, the reaction mixture was extracted with diethyl ether. The extract was washed with water and dried. The solvents were distilled off under reduced pressure and the residue was recrystallized from diethyl ether-hexane. The procedure provided 4-(2'-hydroxy-3',4'-dimethoxy-6'-methylphenyl)butyric acid (formula II-2 wherein R=H$_3$CO, X=H, Y=OH, n=2, in the free form) (0.34 part) as colorless needles melting at 98°–100° C.

Elemental analysis, C$_{13}$H$_{18}$O$_5$— Calculated: C, 61.40; H, 7.14. Found: C, 61.35; H, 7.01.

EXAMPLE 13

9-(2'-Hydroxy-3',4'-dimethoxy-6'-methylbenzoyl)nonanoic acid (formula II-1 wherein R=H$_3$CO, X=H, Y=OH, n=8, in the free form) (0.197 part) was dissolved in methanol saturated with hydrogen chloride gas (7 volume parts) and the solution was stirred at room temperature for 20 minutes. The methanol was distilled off under reduced pressure and the residue was recrystallized from hexane-diethyl ether. The procedure provided methyl 9-(2'-hydroxy-3',4'-dimethoxy-6'-methylbenzoyl)nonanoate (formula II-1 wherein R=H$_3$CO, X=H, Y=OH, n=8, in the form of methyl ester) (0.195 part) as colorless needles melting at 49°–53° C.

Infrared absorption spectrum $\nu_{max}^{KBr}$ cm$^{-1}$: 1740(COOCH$_3$), 1620(CO).

Nuclear magnetic resonance spectrum($\tau$ in deuterochloroform): 8.82–8.13(CH$_2$, multiplet), 7.68(CH$_2$CO, triplet), 7.57(CH$_3$, singlet), 7.10(COCH$_2$, triplet), 6.33(COOCH$_3$, singlet), 6.15(OCH$_3$, singlet), 6.10 (OCH$_3$, singlet), 3.67(ring proton, singlet), −0.03 (OH, singlet).

Elemental analysis, C$_{20}$H$_{30}$O$_6$— Calculated: C, 65.55; H, 8.25. Found: C, 65.58; H, 8.17.

EXAMPLE 14

A solution of methyl 9-(2'-hydroxy-3',4'-dimethoxy-6'-methylbenzoyl)nonanoate (formula II-1 wherein R=H$_3$CO, X=H, Y=OH, n=8, in the form of methyl ester) (0.12 part) in acetic acid (17 volume parts) was shaken with 5% palladium-on-carbon in a current of hydrogen gas at 50°–60° C. The catalyst was removed by filtration and the acetic acid was distilled off under reduced pressure. The residue was subjected to column chromatography on silicic acid (6 parts) and elution was carried out with chloroform. The procedure provided methyl 10-(2'-hydroxy-3',4'-dimethoxy-6'-methylphenyl)decanoate (formula II-2 wherein R=H$_3$CO, X=H, Y=OH, n=8, in the form of methyl ester) (0.09 part) as a colorless oil.

Infrared absorption spectrum $\nu_{max}^{film}$ cm$^{-1}$: 3450(OH), 1740(COOCH$_3$).

Nuclear magnetic resonance spectrum ($\tau$ in deuterochloroform): 8.90-8.13($CH_2$, multiplet), 7.83-7.43(ring $CH_3CH_2CO$, multiplet), 7.73(ring $CH_3$, singlet), 6.37($COOCH_3$, singlet), 6.20($OCH_3$, singlet), 6.15($OCH_3$, singlet), 4.20(OH, singlet), 3.73(ring proton, singlet).

EXAMPLE 15

5-(2'-Hydroxy-3',4',6'-trimethylbenzoyl)pentanoic acid (formula II-1 wherein R=$H_3C$, X=H, Y=OH, n=4, in the free form) (0.048 part) was dissolved in 0.5% NaOH (3.3 volume parts) and, while the solution was stirred at 20° C., potassium nitrosodisulfonate (0.4 part) was added. The mixture was stirred for 10 minutes. Then, under cooling with ice, the reaction mixture was diluted with water (100 volume parts) and rendered acidic with dilute hydrochloric acid. It was then extracted with diethyl ether and the extract was washed with water and dried. The solvent was distilled off under reduced pressure and the residue was then recrystallized from hexane-ethyl acetate (2:1). The procedure provided 2,3,5-trimethyl-6-(5'-carboxyl-1'-oxopentyl)-1,4-benzoquinone (formula I-1 wherein R=$H_3C$, n=4, in the free form) (0.042 part) as yellow needles melting at 96.5°-98.5° C.

EXAMPLE 16

5-(2'-Hydroxy-3',4'-dimethoxy-6'-methylbenzoyl)pentanoic acid (formula II-1 wherein R=$H_3CO$, X=H, Y=OH, n=4, in the free form) (5.7 parts) was oxidized by a procedure similar to that described in Example 15. Recrystallization of the oxidation product from hexane-diethyl ether provided 2,3-dimethoxy-5-methyl-6-(5'-carboxy-1'-oxopentyl)-1,4-benzoquinone (formula I-1 wherein R=$H_3CO$, n=4, in the free form) (3.2 parts) as orange-red crystals melting at 48°-54° C.

Infrared absorption spectrum $\nu_{max}^{KBr}$ $cm^{-1}$: 1710(COOH), 1710(CO),1675, 1655, 1610(quinone).

Nuclear magnetic resonance spectrum ($\tau$ in deuterochloroform): 8.31($CH_2$, multiplet), 8.07($CH_3$, singlet), 7.63($CH_2CO$, multiplet), 7.35($COCH_2$, multiplet), 6.01($OCH_3$, singlet).

Elemental analysis, $C_{15}H_{18}O_7$— Calculated: C, 58.06; H, 5.85. Found: C, 57.89; H, 5.90.

EXAMPLE 17

A mixture of 2,3-dimethoxy-5-methyl-6-(5'-carboxy-1'-oxopentyl)-1,4-benzoquinone (formula I-1 wherein R=$H_3CO$, n=4, in the free form) (0.12 part), toluene (10 volume parts), concentrated hydrochloric acid (1 volume part), water (1 volume part) and zinc amalgam prepared from 1 part zinc was refluxed for 20 hours. After cooling, the reaction mixture was extracted with diethyl ether, washed with water and dried. The solvents were distilled off under reduced pressure to obtain 2,3-dimethoxy-5-methyl-6-(5'-carboxypentyl)benzohydroquinone (formula II-2 wherein R=$H_3CO$, X=Y=OH, n=4, in the free form)

Infrared absorption spectrum $\nu_{max}^{film}$ $cm^{-1}$: 3500(OH), 1715(COOH).

Nuclear magnetic resonance spectrum ($\tau$ in deuterochloroform): 8.75-8.20($CH_2$, multiplet), 7.87($CH_3$, singlet), 7.75-7.27(ring $CH_2$, $CH_2COO$, multiplet), 6.13($OCH_3$, singlet).

EXAMPLE 18

In the presence of 5% palladium-on-carbon and in a current of hydrogen gas, a solution of 2,3,5-trimethyl-6-(5'-carboxy-1'-oxopentyl)-1,4-benzoquinone (formula I-1 wherein R=$H_3C$, n=4, in the free form) (1 part) in acetic acid (200 volume parts) was stirred at 65°-70° C. for 4 hours. The catalyst was filtered off and the filtrate was concentrated under reduced pressure. The procedure provided 2,3,5-trimethyl-6-(5'-carboxypentyl)benzohydroquinone (formula II-2 wherein R=$H_3C$, X=Y=OH, n=4, in the free form) (0.9 part) melting at 145°-153° C.

EXAMPLE 19

2,3-Dimethoxy-5-methyl-6-(5'-carboxy-1'-oxopentyl)-1,4-benzoquinone (formula I-1 wherein R=$H_3CO$, n=4, in the free form) (0.26 part) was dissolved in a mixture of diethyl ether (20 volume parts) and ethyl acetate (20 volume parts) and the solution was shaken with a solution of sodium hydrosulfite (3 parts) in water (50 volume parts). The organic layer was taken, washed with water and dried. The solvents were then removed by distillation under reduced pressure to obtain 2,3-dimethoxy-5-methyl-6-(5'-carbonyl-1'-oxopentyl)benzohydroquinone (formula II-1 wherein R=$H_3CO$, X=Y=OH, n=4, in the free form) (0.25 part) as pale-yellow crystals melting at 110°-115° C.

EXAMPLE 20

2,3,5-Trimethyl-6-(5'-carboxy-1'-oxopentyl)-1,4-benzoquinone (formula I-1 wherein R=$H_3C$, n=4, in the free form) (1 part) was reduced by a procedure similar to that described in Example 19. The procedure provided 2,3,5-trimethyl-6-(5'-carboxy-1'-oxopentyl)benzohydroquinone (formula II-1 wherein R=$H_3C$, X=Y=OH, n=4, in the free form) (0.9 part) as pale-yellow crystals melting at 106°-108° C.

EXAMPLE 21

A diethyl ether solution of 2,3-dimethoxy-5-methyl-6-(5'-carboxypentyl)-1,4-benzoquinone (formula I-2 wherein R=$H_3CO$, n=4, in the free form) (0.84 part) was shaken with a solution of sodium hyrosulfite (10 parts) in water (100 volume parts). The ethereal layer was taken and treated in the conventional manner to obtain 2,3-dimethoxy-5-methyl-6-(5'-carboxypentyl)benzohydroquinone (formula II-2 wherein R=$H_3CO$, X=Y=OH, n=4, in the free form) (0.69 part) as a colorless oil.

EXAMPLE 22

2,3,5-Trimethyl-6-(5'-carboxypentyl)-1,4-benzoquinone (formula I-2 wherein R=$H_3C$, n=4, in the free form) was reduced by a procedure similar to that described in Example 21 to obtain 2,3,5-trimethyl-6-(5'-carboxypentyl)hydroquinone (formula II-2 wherein R=$H_3C$, X=Y=OH, n=4, in the free form) as colorless crystals melting at 145°-153° C.

EXAMPLE 23

6-(2'-Hydroxy-3',4'-dimethoxy-6'-methylphenyl)hexanoic acid (formula II-2 wherein R=$H_3CO$, X=H, Y=OH, n=4, in the free form) was dissolved in a 5% solution of sodium hydroxide, followed by the addition of an aqueous solution of potassium persulfate. The mixture was stirred at room temperature for 24 hours. The reaction mixture was rendered acidic with hydrochloric acid and extracted with diethyl ether. The ethereal extract was then treated in the conventional manner to obtain 2,3-dimethoxy-5-methyl-6-(5'-carboxypentyl)benzohydroquinone (formula II-2 wherein e.g. magnesium and calcium, aluminum salts, and amine salts, e.g. ammonium, trimethylamine and triethylamine salts.

The compounds (I) and their salts thus obtainable are novel and have physiologic host defense control action, especially immuno-potentiating action; smooth muscle relaxant action; and other action, and accordingly these compounds are of use, for example, as physiologic host defense control agents, especially immuno-potentiating agents for mammals including human beings.

Among the compounds (I), the compounds (I-1) can be used also as the intermediate for producing the compound (I-2).

Further, among the compounds (I), the compounds (I-2) wherein R is lower alkyl and a compound (I-2) wherein R is lower alkoxy and n is not less than 3 have excellent action to stabilize the lysosomal membranes of cells; and the compounds (I-2) wherein R is lower alkoxy and n is not more than 2 have excellent action to labilize the lysosomal membranes of cells.

Furthermore the compounds (I-1) and (I-3) also have excellent action to the lysosomal membranes of cells.

The compounds (I) and their salts are administered orally or non-orally to mammals including human beings, either by themselves or in admixture with a suitable carrier, for example in such dosage forms as powders, granules, tablets and injections.

Pharmaceutical compositions containing one or more of the compounds (I) and their salts can be prepared by per se conventional methods for the preparation of powder, capsules, tablets, granules, injections, and the like. The choice of carriers may be determined depending upon the route of administration, the solubility of the compounds and so on.

While the dosage of the compounds (I) may be chosen depending upon the species of host, the purpose of administration and the route of administration, when used as immuno-potentiating agents for mammals, for instance, the preferred parental dose is about 50 $\mu$g–50 mg./kg., advantageously 1–25 mg/kg., per injection.

The compounds (II) and their salts, (III) and (IV) thus obtainable are novel, and also have physiologic host defense control action; action to lysosomal membranes of cells and so on similar to those set forth in connection with the compounds (I), and, as such, can be use as medicines in the same manner as the compounds (I).

Further, the compounds (II) can be used also as intermediates for producing the compounds (I).

The following Examples are intended merely to illustrate presently preferred embodiments of the present invention and not to restrict the scope of this invention.

Throughout the foregoing description as well as in the following Examples and Claims, "$\mu$g.", "mg.", "kg.", "ml.", "° C" and "N" respectively refer to "microgram(s)", "milligram(s)", "kilogram(s)", "milliliter(s)", "degrees centrigrade" and "Normal(s)". The word "part(s)" is based on weight unless otherwise noted and the relationship between "part(s)" and "volume part(s)" corresponds to that between "gram(s)" and "milliliter(s)".

EXAMPLE 1

(1) To a solution of 2,3,5-trimethylphenol(formula VII wherein R=H$_3$C, X=H, Y=OH) (1.4 part) in tetrachloroethane (10 volume parts), there was added a solution of aluminum chloride dust (3.5 parts) and ethyl 5-chloroformylpentanoate (3 parts) in tetrachloroethane (5 volume parts) at 0° C. and in a current of nitrogen gas and the mixture was heated at 110°–120° C. for 17 hours. To the reaction mixture was added cold water (50 volume parts) and the dilution was acidified with dilute hydrochloric acid and extracted with chloroform (200 volume parts). The residue (2.7 parts) obtained from the extract was subjected to column chromatography on silicic acid (60 parts) and eluted with chloroform-diethyl ether (20:1) (300 volume parts). The eluate was evaporated to dryness and the residue was recrystallized from ethanol. The procedure provided colorless needles of ethyl 5-(2'-hydroxy-3',4',6'-trimethylbenzoyl)pentanoate (formula II-1 wherein R=H$_3$C, X=H, Y=OH, n=4, in the form of ethyl ester) (1.9 part) melting at 72°–73° C.

Infrared absorption spectrum $\nu_{max}^{KBr}$ cm$^{-1}$: 3450(OH), 1720(COOC$_2$H$_5$), 1610(CO).

Nuclear magnetic resonance spectrum ($\tau$ in deuterochloroform): 8.76(CH$_3$, triplet), 8.5–8.1(CH$_2$, multiplet), 8.0–7.6 (CH$_2$, multiplet), 7.89(ring CH$_3$, singlet), 7.78(ring CH$_3$, singlet), 7.50(ring CH$_3$, singlet), 7.25–7.00 (CH$_2$, multiplet), 5.88(OCH$_2$, quartet), 3.48(ring proton, singlet).

Elemental analysis, C$_{17}$H$_{24}$O$_4$— Calculated: C, 69.83; H, 8.27. Found: C, 69.78; H, 8.44.

(2) To a solution of the above product (0.61 part) in aqueous acetone (acetone-water=5:1)(12 volume parts) was added dropwise a 10% aqueous solution of sodium hydroxide (10 volume parts) under stirring at room temperature. After stirring for 30 minutes, the reaction mixture was cooled to 0° C. and cold water (50 volume parts) was added. The dilution was rendered acidic with cold dilute hydrochloric acid and the resultant white precipitate was recrystallized from ethanol. The procedure provided colorless needles of 5-(2'-hydroxy-3',4',6'-trimethylbenzoyl)pentanoic acid (formula II-1 wherein R=H$_3$C, X=H, Y=OH, n=4, in the free form) (0.428 part) melting at 146°–148° C., Infrared absorption spectrum $\nu_{max}^{KBr}$ cm$^{-1}$: 3430(OH), 1700(COOH), 1605(CO).

Nuclear magnetic resonance spectrum ($\tau$ in deuterochloroform): 8.5–8.0(CH$_2$, multiplet), 8.0–7.3(CH$_2$, multiplet), 7.88(ring CH$_3$, singlet), 7.78(ring CH$_3$, singlet), 7.47(ring CH$_3$, singlet), 7.2–6.9(CH$_2$, multiplet), 3.47(ring proton, singlet).

Elemental analysis, C$_{15}$H$_{20}$O$_4$— Calculated: C, 68.16; H, 7.63. Found: C, 67.95; H, 7.92.

EXAMPLE 2

(1) 2,3,5-Trimethylphenol (formula VII wherein R=H$_3$C, X=H, Y=OH)(0.9 part), aluminum chloride (2.1 parts) and ethyl 6-chloroformylhexanoate (1.3 part) were treated as in Example 1 (1). The procedure provided colorless needles of ethyl 6-(2'-hydroxy-3',4',6'-trimethylbenzoyl)hexanoate (formula II-1 wherein R=H$_3$C, X=H, Y=OH, n=5, in the form of ethyl ester) (1.5 part) melting at 47°–48° C.

Infrared absorption spectrum $\nu_{max}^{KBr}$ cm$^{-1}$: 1735(COOC$_2$H$_5$), 1610(CO).

Nuclear magnetic resonance spectrum ($\tau$ in deuterochloroform): 8.76(CH$_3$, triplet), 8.7–8.0(CH$_2$, multiplet), 8.0–7.4(CH$_2$, multiplet), 7.88(ring CH$_3$, singlet), 7.78(ring CH$_3$, singlet), 7.49(ring CH$_3$, singlet), 7.01(CH$_2$, triplet), 5.87(OCH$_2$, quartet), 3.47(ring proton, singlet).

Elemental analysis, C$_{18}$H$_{26}$O$_4$— Calculated: C, 70.56; H, 8.55. Found: C, 70.23; H, 8.72.

(2) By a procedure similar to that described in Example 1 (2), the above product (1 part) was hydrolyzed to obtain colorless needles of 6-(2'-hydroxy-3',4',6'-trimethylbenzoyl)hexanoic acid (formula II-1 wherein R=H$_3$C, X=H, Y=OH, n=5, in the free form)(0.8 part) which melted at 119°–125° C.

Infrared absorption spectrum $\nu_{max}^{KBr}$ cm$^{-1}$: 1710(COOH), 1610(CO).

Nuclear magnetic resonance spectrum ($\tau$ in deuterochloroform): 8.7–8.0(CH$_2$, multiplet), 8.0–7.3(CH$_2$, multiplet), 7.86(ring CH$_3$, singlet), 7.75(ring CH$_3$, singlet), 7.47(ring CH$_3$, singlet), 7.06(CH$_2$, triplet), 3.46 ring proton, singlet)

Elemental analysis, C$_{16}$H$_{22}$O$_4$— Calculated: C, 69.04; H, 7.97. Found: C, 69.12; H, 7.75.

EXAMPLE 3

(1) 2,3,5-Trimethylphenol (formula VII wherein R=H$_3$C, X=H, Y=OH)(1.5 part), aluminum chloride (3.5 parts) and ethyl 9-chloroformylnonanoate (3 parts) were treated together in the same manner as Example 1 (1).

The procedure provided ethyl 9-(2'-hydroxy-3',4',6'-trimethylbenzoyl)nonanoate (formula II-1 wherein R=H$_3$C, X=H, Y=OH, n=8, in the form of ethyl ester) as colorless needles (2 parts) melting at 48°–50° C.

Infrared absorption spectrum $\nu_{max}^{KBr}$ cm$^{-1}$: 3450(OH), 1735(COOC$_2$H$_5$), 1610(CO).

Nuclear magnetic resonance spectrum($\tau$ in deuterochloroform): 9.0–8.0(CH$_2$, multiplet), 8.76(CH$_3$, triplet), 8.0–7.4(CH$_2$, multiplet), 7.88(ring CH$_3$, singlet), 7.78(ring CH$_3$, singlet), 7.49(ring CH$_3$, singlet), 7.04(CH$_2$, triplet), 5.87(OCH$_2$, quartet), 3.47(ring proton, singlet).

Elemental analysis, C$_{21}$H$_{32}$O$_4$— Calculated: C, 72.38; H, 9.26. Found: C, 72.32; H, 9.56.

(2) The above product (1.4 part) was hydrolyzed in the same manner as Example 1 (2). The procedure provided 9-(2'-hydroxy-3',4',6'-trimethylbenzoyl)nonanoic acid (formula II-1 wherein R=H$_3$C, X=H, Y=OH, N=8, in the free form) as colorless needles (1.2 part) melting at 97°–100° C.

Infrared absorption spectrum $\nu_{max}^{KBr}$ cm$^{-1}$: 3450(OH), 1710(COOH), 1610(CO).

Nuclear magnetic resonance spectrum ($\tau$ in deuterochloroform): 8.9–8.0(CH$_2$, multiplet), 8.0–7.3(CH$_2$, multiplet), 7.85(ring CH$_3$, singlet), 7.77(ring CH$_3$, singlet), 7.47(ring CH$_3$, singlet), 7.07(CH$_2$, triplet), 3.45(ring proton, singlet).

Elemental analysis, C$_{19}$H$_{28}$O$_4$— Calculated: C, 71.22; H, 8.81. Found: C, 71.10; H, 8.97.

EXAMPLE 4

(1) Under cooling with ice, aluminum chloride (4.08 parts) was added in small portions to a mixed solution of ethyl 9-chloroformylnonanoate (3.52 parts) and 3,4,5-trimethoxytoluene(formulaVII wherein R=H$_3$CO, X=H, Y=H$_3$CO) (2.21 parts) in nitrobenzene (20 volume parts). The mixture was stirred at 0° C. for 16 hours and, then, at room temperature for 1.5 hours. The reaction mixture was rendered acidic with dilute hydrochloric acid and extracted with diethyl ether. By a procedure similar to that described in Example 1 (2), the extract was hydrolyzed and subjected to column chromatography on silicic acid. The fraction eluted by benzenediethyl ether (9:1) yielded 9-(2',3',4'-trimethoxy-6'-methylbenzoyl)nonanoic acid (formula II-1 wherein R=H$_3$CO, X=H, Y=OCH$_3$, n=8, in the free form) (1.82 part). From the fraction eluted by benzene-diethyl ether (5.7:1), there was obtained 9-(2'-hydroxy-3',4'-dimethoxy-6'-methylbenzoyl)nonanoic acid (formula II-1, R=H$_3$CO, X=H, Y=OH, n=8, in the free form) (0.67 part) as colorless needles melting at 75°–76.5° C.

Elemental analysis, C$_{19}$H$_{28}$O$_6$— Calculated: C, 64.75; H, 8.01. Found: C, 64.87; H, 8.06.

EXAMPLE 5

3,4,5-Trimethoxytoluene(formula VII wherein R=H$_3$CO, X=H, Y=H$_3$CO)(2.09 parts) and ethyl 5-chloroformylpentanoate (2.66 parts) were treated in the same manner as Example 4. The procedure provided 5-(2'-hydroxy-3',4'-dimethoxy-6'-methylbenzoyl)pentanoic acid (formula II-1 wherein R=H$_3$CO, X=H, Y=OH, n=4, in the free form)(1.97 part) as pale-brown needles melting at 111°–112° C.

Infrared absorption spectrum $\nu_{max}^{KBr}$ cm$^{-1}$: 3250(OH), 1740(COOH), 1615(CO).

Elemental analysis, C$_{15}$H$_{20}$O$_6$— Calculated: C, 60.80; H, 6.80. Found: C, 60.69; H, 6.75.

EXAMPLE 6

3,4,5-Trimethoxytoluene (formula VII wherein R=H$_3$CO, X=H, Y=H$_3$CO) (3.65 parts) and succinic anhydride (2.4 parts) were dissolved in a mixture of nitrobenzene (10 volume parts) and tetrachloroethane (30 volume parts) and, under cooling with ice and stirring. To the mixture, aluminum chloride dust (7.2 parts) was added in small portions. The mixture was allowed to stand at room temperature for 4 days and, following the addition of dilute hydrochloric acid, it was extracted with diethyl ether. The ethereal layer was then extracted with a 10% solution of sodium carbonate. The sodium carbonate extract was washed with diethyl ether to remove the nitrobenzene and tetrachloroethane and the water layer was rendered acidic with dilute hydrochloric acid. The resulting oil precipitate was extracted with ethyl acetate, washed with water and dried. The solvent was distilled off under reduced pressure.

The residue was then recrystallized from methanol, whereupon 3-(2'-hydroxy-3',4'-dimethoxy-6'-methylbenzoyl)propionic acid (formula II-1 wherein R=H$_3$CO, X=H, Y=OH, n=2, in the free form) (1 part) was obtained as pale-yellowish crystals melting at 145°–147° C.

Elemental analysis, C$_{13}$H$_{16}$O$_6$—
Calculated: C, 58.20; H, 6.01. Found: C, 58.07; H, 5.98.

EXAMPLE 7

To 5-(2'-hydroxy-3',4',6'-trimethylbenzoyl)pentanoic acid (formula II-1 wherein R=H$_3$C, X=H, Y=OH, n=4, in the free form) (0.262 part) were added water (16 volume parts), toluene (20 volume parts), concentrated hydrochloric acid (4 volume parts) and zinc amalgam prepared from 2 parts of zinc. The mixture was refluxed for 16 hours, during which time concentrated hydrochloric acid (6 volume parts) was added in three portions. After cooling, the reaction mixture was diluted with water and extracted with diethyl ether. The extract was washed with water and dried. The solvents were distilled off under reduced pressure to obtain 6-(2'-hydroxy-3',4',6'-trimethylphenyl)hexanoic acid (formula II-2 wherein R=H$_3$C, X=H, Y=OH, n=4, in the free form)(0.251 part) as colorless needles melting at 96°–108° C.

R=H₃CO, X=Y=OH, n=4, in the free form) as a colorless oil.

EXAMPLE 24

6-(2'-Hydroxy-3',4',6'-trimethylphenyl)hexanoic acid (formula II-2 wherein R=H₃C, X=H, Y=OH, n=4, in the free form) was subjected to a procedure similar to that described in Example 23. The procedure provided 2,3,5-trimethyl-6-(5'-carboxypentyl)benzohydroquinone (formula II-2 wherein R=H₃C, X=Y=OH, n=4, in the free form) as colorless crystals melting at 145°-153° C.

EXAMPLE 25

Potassium nitrosodisulfonate (0.9 part) was added to a solution of 6-(2'-hydroxy-3',4',6'-trimethylphenyl)hexanoic acid (formula II-2 wherein R=H₃C, X=H, Y=OH, n=4, in the free form) (0.111 part) in 1% sodium hydroxide (5 volume parts) and water (3 volume parts) and the mixture was stirred at room temperature for 30 minutes. Then, the reaction mixture was cooled to 0° C. and, following the addition of cold water (50 volume parts), it was rendered acidic with dilute hydrochloric acid, whereupon a yellow precipitate was obtained. Recrystallization of this precipitate from hexane-ethyl acetate (10:1) provided 2,3,5-trimethyl-6-(5'-carboxypentyl)-1,4-benzoquinone (formula I-2 wherein R=H₃C, n=4, in the free form) (0.11 part) as yellow needles melting at 81°-82° C.

Infrared absorption spectrum $\nu_{max}^{KBr}$ cm⁻¹: 1705(COOH), 1640(quinone).

Nuclear magnetic resonance spectrum ($\tau$ in deuterochloroform): 8.8-8.1(CH₂, multiplet), 8.00(ring CH₃, singlet), 7.9-7.3(CH₂, multiplet).

Elemental analysis, C₁₅H₂₀O₄— Calculated: = C, 68.16; H, 7.63. Found: = C, 68.19; H, 7.61.

EXAMPLE 26

7-(2'-Hydroxy-3',4',6'-trimethylphenyl)heptanoic acid (formula II-2 wherein R=H₃C, X=H, Y=OH, n=5, in the free form) (1.02 part) was oxidized by a procedure similar to that described in Example 25. The procedure provided 2,3,5-trimethyl-6-(6'-carboxyhexyl)-1,4-benzoquinone(formula I-2 wherein R=H₃C, n=5 in the free form) (0.82 part) as yellow needles melting at 71°-72° C.

Infrared absorption spectrum $\nu_{max}^{KBr}$ cm⁻¹: 1710(COOH), 1640(quinone).

Nuclear magnetic resonance spectrum ($\tau$ in deuterochloroform): 8.9-8.1(CH₂, multiplet), 7.98(ring CH₃, singlet), 7.9-7.3(CH₂, multiplet).

Elemental analysis, C₁₆H₂₂O₄— Calculated: C, 69.04; H, 7.97. Found: C, 69.08; H, 8.04.

EXAMPLE 27

10-(2'-Hydroxy-3',4',6'-trimethylphenyl)decanoic acid (formula II-2 wherein R=H₃C, X=H, Y=OH, n=8, in the free form) (4 parts) was oxidized by a procedure similar to that described in Example 25. The procedure provided 2,3,5-trimethyl-6-(9'-carboxynonyl)-1,4-benzoquinone (formula I-2 wherein R=H₃C, n=8, in the free form) (1.47 part) as a yellow oil.

Infrared absorption spectrum $\nu_{max}^{film}$ cm⁻¹: 1705(COOH), 1640(quinone).

Nuclear magnetic resonance spectrum($\tau$ in deuterochloroform): 8.9-8.1(CH₂, multiplet), 8.0(ring CH₃, singlet), 8.0-7.3(CH₂, multiplet)

Elemental analysis, C₁₉H₂₈O₄— Calculated: C, 71.22; H, 8.81. Found: C, 71.19; H, 8.80.

EXAMPLE 28

A solution of potassium nitrosodisulfonate (0.8 part) in water (10 volume parts) was added to a solution of 10-(2'-hydroxy-3',4'-dimethoxy-6'-methylphenyl)-decanoic acid (formula II-2 wherein R=H₃CO, X=H, Y=OH, n=8, in the free form) (0.097 part) in a mixture of 1% sodium hydroxide (0.67 volume part) and acetone (2 volume parts) and the mixture was stirred at room temperature for 2 hours. The reaction mixture was rendered acidic with dilute hydrochloric acid and extracted with diethyl ether. The extract was washed with water and dried, followed by evaporation to dryness. The procedure provided 2,3-dimethoxy-5-methyl-6-(9'-carboxynonyl)-1,4-benzoquinone (formula I-2 wherein R=H₃CO, n=8, in the free form) (0.099 part) as orange-colored needles melting at 59°-60.5° C.

Nuclear magnetic resonance spectrum ($\tau$ in deuterochloroform): 8.82-8.25 (CH₂, multiplet), 8.00(ring CH₃, singlet), 7.65(ring CH₂, CH₂CO, triplet), 6.03(OCH₃, singlet), 0.22(COOH, broad).

Elemental analysis, C₁₉H₂₈O₆— Calculated: C, 64.75; H, 8.01. Found: C, 64.69; H, 8.11.

EXAMPLE 29

6-(2'-Hydroxy-3',4'-dimethoxy-6'-methylphenyl)hexanoic acid (formula II-2 wherein R=H₃CO, X=H, Y=OH, n=4 in the free form) (8.4 parts) was oxidized by a procedure similar to that described in Example 28. The procedure provided 2,3-dimethoxy-5-methyl-6-(5'-carboxypentyl)-1,4-benzoquinone (formula I-2 wherein R=H₃CO, n=4, in the free form) (7.6 parts) as orange-colored granules melting at 82°-86° C.

Nuclear magnetic resonance spectrum ($\tau$ in deuterochloroform): 8.73-8.20(CH₂, multiplet), 7.97(ring CH₃, singlet), 7.60(ring CH₂, CH₂CO, triplet), 6.00(OCH₃, singlet), −0.55(COOH, broad)

Elemental analysis, C₁₅H₂₀O₆— Calculated: C, 60.80; H, 6.80. Found: C, 60.60; H, 6.81.

EXAMPLE 30

4-(2'-Hydroxy-3',4'-dimethoxy-6'-methylphenyl)-butyric acid (formula II-2 wherein R=H₃CO, X=H, Y=OH, n=2, in the free form) (2.54 parts) was oxidized by a procedure similar to that described in Example 28. The procedure provided 2,3-dimethoxy-5-methyl-6-(3'-carboxypropyl)-1,4-benzoquinone (formula I-2 wherein R=H₃CO, n=2, in the free form) (2.2 parts) as orange-colored needles melting at 74°-75° C.

Elemental analysis, C₁₃H₁₆O₆— Calculated: C, 58.20; H, 6.01. Found: C, 58.03; H, 5.77.

EXAMPLE 31

To a well stirred solution of methyl 10-(2'-hydroxy-3'-4'-dimethoxy-6'-methylphenyl)-decanoate (formula II-2 wherein R=H₃CO, X=H, Y=OH, n=8 in the form of methyl ester) (3.3 parts) in acetone (50 volume parts) were added potassium nitrosodisulfonate (10 parts) and potassium biphosphate (10 parts). The procedure provided 2,3-dimethoxy-5-methyl-6-(9'-methoxycarbonylnonyl)-1,4-benzoquinone (formula I-2 wherein R=H₃CO, n=8, in the form of methyl ester) (1.5 part) as orange-colored needles melting at 37°-37.5° C.

Elemetal analysis, C₂₀H₃₀O₆— Calculated: C, 65.55; H, 8.25. Found: C, 65.44; H, 8.36.

EXAMPLE 32

To 2,3-dimethoxy-5-methyl-6-(5'-carboxypentyl)benzohydroquinone (formula II-2 wherein $R=H_3CO$, $X=Y=OH$, $n=4$ in the free form) (0.08 part) was added a 10% solution of ferric chloride (150 volume parts), and the mixture was shaken. It was then extracted with diethyl ether and the extract was washed with water and dried. The solvent was then distilled off under reduced pressure. The residue was subjected to column chromatography on silicic acid (10 parts) and the fraction eluted with chloroform-ethanol (49:1) was recrystallized from diethyl ether-hexane. The procedure provided 2,3-dimethyoxy-5-methyl-6-(5'-carboxypentyl)-1,4-benzoquinone (formula I-2 wherein $R=H_3CO$, $n=4$, in the free form) (0.067 part) as orange-colored crystals melting at 83°–85° C.

EXAMPLE 33

A solution of 2,3,5-trimethyl-6-(5'-carboxypentyl)-benzoquinone (formula II-2 wherein $R=H_3C$, $X=Y=OH$, $n=4$, in the free form) (0.9 part) in diethyl ether was shaken with a 10% solution of ferric chloride. The reaction product was separated and purified by procedures similar to those described in Example 32 to obtain 2,3,5-trimethyl-6-(5'-carboxypentyl)-1,4-benzoquinone (formula I-2 wherein $R=H_3C$, $n=4$, in the free form) (0.6 part) as yellow needles melting at 81°–82° C.

EXAMPLE 34

The acid chloride (1.01 part) synthesized from 2,3,5-trimethyl-6-(5'-carboxypentyl)-1,4-benzoquinone (formula I-2 wherein $R=H_3C$, $n=4$, in the free form) (1 part) and oxalyl chloride (5 volume parts) was dissolved in anhydrous benzene (10 volume parts) and the solution was added dropwise to a solution of salicylaldehyde (0.6 part) in pyridine (10 volume parts) at 25° C. After stirring for 2.5 hours, the reaction mixture was diluted with cold water (300 volume parts) and rendered acidic with dilute hydrochloric acid. It was then extracted twice with diethyl ether (300 volume parts). The extracts were pooled, washed with water and dried. The solvent was then distilled off under reduced pressure and the residue was subjected to column chromatography on silica gel. Elution with chloroform provided a yellow oil of 2,3,5-trimethyl-6-[5'-(o-formylphenyloxycarbonyl) pentyl]-1,4-benzoquinone (formula I-2 wherein $R=H_3C$, $n=4$, in the form of o-formylphenolate) (1.3 part). To a cooled, stirred solution of this product (1.1 part) in acetone (25 volume parts) was added standard Jones reagent (2 volume parts). The solution was stirred for 100 minutes, after which it was diluted with cold water (500 volume parts), followed by extraction with ethyl acetate (500 volume parts). The extract was washed with water and dried. The solvent was then distilled off under reduced pressure and the residue was purified by column chromatography on silica gel (50 parts). The procedure provided a yellow oil of 2,3,5-trimethyl-6-[5'-(o-carboxyphenyloxycarbonyl) pentyl]-1,4-benzoquinone (formula I-2 wherein $R=H_3C$, $n=4$, in the form of o-carboxyphenolate) (1.1 part).

EXAMPLE 35

A mixture of 2,3,5-trimethyl-6-(5'-carboxypentyl)-1,4-benzoquinone (formula I-2 wherein $R=H_3C$, $n=4$, in the free form) (0.2 part), benzyl chloride (0.4 part), silver oxide (0.283 part) and benzene was refluxed for 19 hours. The insolubles were filtered off and the filtrate was concentrate under reduced pressure. The concentrate was then subjected to column chromatography on silica gel to recover a yellow oil of 2,3,5-trimethyl-6-(5'-benzyloxycarbonylpentyl)-1,4-benzoquinone (formula I-2 wherein $R=H_3C$, $n=4$, in the form of benzylester) (0.189 part).

EXAMPLE 36

2,3-Dimethoxy-5-methyl-6-(9'-carboxynonyl)-1,4-benzoquinone (formula I-2 wherein $R=H_3CO$, $n=8$, in the free form) (4 parts) was esterified with methanol (500 volume parts) saturated with hydrogen chloride gas in a manner similar to that described in Example 13. The procedure provided 2,3-dimethoxy-5-methyl-6-(9'-methoxycarbonylnonyl)-1,4-benzoquinone (formula I-2 wherein $R=H_3CO$, $n=8$, in the form of methyl ester) (4.2 parts) as orange-colored needles melting at 37°–37.5° C.

EXAMPLE 37

To a methanolic solution of 2,3-dimethoxy-5-methyl-6-(9'-methoxycarbonylnonyl)-1,4-benzoquinone (formula I-2 wherein $R=H_3CO$, $n=8$, in the form of methylester) (0.17 part) and pyrogallol (1.6 part) was added a 10% methanolic solution of potassium hydroxide (40 volume parts) and the mixture was refluxed for 2 hours. The reaction mixture was rendered acidic with hydrochloric acid and extracted with diethyl ether. The ethereal extract was shaken together with a 10% aqueous solution of ferric chloride and the ethereal layer was taken, washed with water and dried. The diethyl ether was distilled off under reduced pressure to recover 2,3-dimethoxy-5-methyl-6-(9'-carboxynonyl)-1,4-benzoquinone (formula I-2 wherein $R=H_3CO$, $n=8$, in the free form) (0.08 part).

EXAMPLE 38

9-(2',3',4'-Trimethoxy-6'-methylbenzoyl)nonanoic acid (formula II-1 wherein $R=Y=H_3CO$, $X=H$, $n=8$, in the free form) (0.09 part) was reduced with zinc amalgam (0.2 part) by a procedure similar to that described in Example 10 and oxidized with 30% hydrogen peroxide (10 volume parts) in acetic acid. Following the addition of water, the reaction mixture was extracted with diethyl ether (500 volume parts) and the extract was washed with water and dried. The ether was then removed by distillation. The procedure provided 2,3-dimethoxy-5-methyl-6-(9'-carboxynonyl)-1,4-benzoquinone (formula I-2 wherein $R=H_3CO$, $n=8$, in the free form).

EXAMPLE 39

To a solution of 2,3-dimethoxy-5-methyl-1,4-benzoquinone (formula V wherein $R=H_3CO$) (3.64 parts) in acetic acid (20 volume parts), there was added disebacoyl peroxide diethyl ester (9.2 parts) in small portions at 85° C. The mixture was further stirred at 85° C. for 2 hours. After cooling, water was added to the reaction mixture, followed by extraction with diethyl ether. The ethereal extract was washed with a saturated aqueous solution of sodium hydrogen carbonate and dried over anhydrous sodium sulfate. The diethyl ether was then distilled off under reduced pressure. The resulting orange-colored oily residue was column-chromatographed on silica gel, and elution was carried out with hexane-diethyl ether. The procedure provided 2,3- dimethoxy-5-methyl-6-(8'-ethoxycarbonyloctyl)-1,4-benzoquinone (formula I-2 wherein R=H₃CO, n=7, in the form of ethylester) (1.79 part) as an orange-colored oil.

Infrared absorption spectrum $\nu_{max}^{film}$ cm⁻¹: 1730(ester), 1660, 1650, 1615 (quinone).

Nuclear magnetic resonance spectrum (τ in carbon tetrachloride): 8.76 (CH₃, triplet), 8.66(CH₂, broad), 8.04 (ring CH₃, singlet), 7.77(ring CH₂, triplet), 7.80-7.37 (CH₂COO, broad), 6.05(CH₃O, singlet). 5.95(COOCH₂, quartet)

Elemental analysis, C₂₀H₃₀O₆ — Calculated: C, 65.55; H, 8.25. Found: C, 65.02; H, 8.07.

To a solution of 2,3-dimethoxy-5-methyl-6-(8'-ethoxycarbonyloctyl)-1,4-benzoquinone (formula I-2 wherein R=H₃CO, n=7, in the form of ethylester) (0.8 part) in diethyl ether (10 volume parts), followed by the addition of a 30% solution (20 volume parts) of potassium hydroxide containing sodium hydrosulfite. The mixture was refluxed for 1 hour. After cooling, the reaction mixture was rendered acidic with hydrochloric acid and extracted with diethyl ether. The ethereal extract was washed with water and shaken together with a solution of ferric chloride. The ethereal layer was washed with water and dried over anhydrous sodium sulfate. The diethyl ether was distilled off under reduced pressure and the resulting residue was crystallized from diethyl ether-hexane. The procedure provided 2,3-dimethoxy-5-methyl-6-(8'-carboxyoctyl)-1,4-benzoquinone (formula I-2 wherein R=H₃CO, n=7, in the free form) (0.53 part) as orange-colored needles melting at 39°-40.5° C.

Elemental analysis, C₁₈H₂₆O₆— Calculated: C, 63.88; H, 7.74. Found: C, 63.60; H, 7.88.

EXAMPLE 40

2,3,5-Trimethyl-1,4-benzoquinone (formula V wherein R=H₃C) (1 part) was reacted with disuccinoyl peroxide dimethyl ester (1.4 part) by a procedure similar to that described in Example 39. The procedure provided 2,3,5-trimethyl-6-(2'-methoxycarbonylethyl)-1,4-benzoquinone (formula I-2 wherein R=H₃C, n=1, in the form of methyl ester) (0.55 part) as a yellow oil.

Infrared absorption spectrum $\nu_{max}^{film}$ cm⁻¹: 1740(ester), 1640(quinone).

Nuclear magnetic resonance spectrum (τ in deuterochloroform): 8.02 (ring CH₃, singlet), 7,95 (ring CH₃, singlet), 7.53 (CH₂COO, triplet), 7.18 (ring CH₂, triplet), 6.50 (COOCH₃, singlet).

The above product (0.082 part) was hydrolyzed in the same manner as Example 39 and the resulting yellow oil was crystallized from diethyl ether-hexane. The procedure provided 2,3,5-trimethyl-6-(2'-carboxyethyl)-1,4-benzoquinone (formula I-2 wherein R=H₃C, n=1, in the free form) (0.058 part) as pale yellowish needles melting at 112°-114° C.

Elemental analysis, C₁₂H₁₄O₄— Calculated: C, 64.85; H, 6.35. Found: C, 64.84; H, 6.32.

EXAMPLE 41

To a solution of 2,3-dimethoxy-5-methyl-1,4-benzoquinone (formula V wherein R=H₃CO) (0.91 part) in acetic acid (10 volume parts) was added disuccinoyl peroxide (2 parts) at 90° C. and the mixture was heated at the same temperature for 4 hours.

Thereafter, the reaction mixture was treated in the same manner as Example 39 to obtain 2,3-dimethoxy-5-methyl-6-(2'-carboxyethyl)-1,4-benzoquinone (formula I-2 wherein R=H₃CO, n=1, in the free form) (0.4 part) as orange-red crystals melting at 122°-124° C.

Elemental analysis, C₁₂H₁₄O₆— Calculated: C, 56.69; H, 5.55. Found: C, 56.91; H, 5.24.

EXAMPLE 42

A solution of ethyl 5-(2'-hydroxy-3',4',6'-trimethylbenzoyl)pentanoate (formula II-1 wherein R=H₃C, X=H, Y=OH, n=4, in the form of ethyl ester) (0.4 part) in tetrahydrofuran (100 volume parts) was reduced with lithium aluminum hydride (0.5 part) under warming for 1 hour. The reaction mixture was quenched with ethyl acetate followed by the addition of saturated aqueous sodium sulfate (5 volume parts) solution. After removal of the resulting inorganic salt by filtration, the filtrate was condensed in vacuo to dryness. The residue was crystallized from diethyl ether to give 1-(2'-hydroxy-3',4',6'-trimethylphenyl)-1,6-hexanediol (formula III-3 wherein R=H₃C, X=H, Y=OH, n=4, in the free form) (0.32 part) as colorless needles melting at 135°-136° C.

Elemental analysis C₁₅H₂₄O₃— Calculated: C, 71.39; H, 9.59. Found: C, 71.38; H, 9.54.

EXAMPLE 43

To a well stirred suspension of lithium aluminum hydride (2 parts) in dry tetrahydrofuran (50 volume parts) was added a solution of 5-(2'-hydroxy-3',4',6'-trimethylbenzoyl)pentanoic acid (formula II-1 wherein R=H₃C, X=H, Y=OH, n=4, in the free form) in dry tetrahydrofuran (10 volume parts) at room temperature. After being stirred under reflux for 2 hours, the mixture was cooled to 0° C., acidified with cold dilute hydrochloric acid, and extracted with ethyl acetate. The ethyl acetate extract was washed with water, dried over anhydrous sodium sulfate, and concentrated in vacuo. The resulting residue was subjected to column chromatography on silica gel and eluted with carbon tetrachloride-acetone (5:1). From the 1st fraction, 6-hydroxy-6-(2'-hydroxy-3',4',6'-trimethylphenyl)hexanoic acid (formula II-3 wherein R=H₃C, X=H, Y=OH, n=4, in the free form) (0.45 part) was obtained as colorless needles melting at 165°-166° C.

Elemental analysis, C₁₅H₂₂O₄— Calculated: C, 67.64; H, 8.33. Found: C, 67.63; H, 8.13.

From the 2nd fraction, 1-(2'-hydroxy-3',4',6'-trimethylphenyl)-1,6-hexanediol (formula III-3 wherein R=H₃C, X=H, Y=OH, n=4, in the free form) (2.5 parts) was obtained. This compound was identified with the product obtained in Example 42.

EXAMPLE 44

To a solution of 6-hydroxy-6-(2'-hydroxy-3',4',6'-trimethylphenyl)hexanoic acid (formula III-3 wherein R=H₃C, X=H, Y=OH, n=4, in the free form) (0.158 part) in 5% sodium hydroxide solution (2 volume parts) and water (7 volume parts) was added Fremy's salt (1 part) at room temperature with stirring. After being stirred for 1 hour, the mixture was cooled to 0° C., acidified with cold dilute hydrochloric acid, and extracted with ethyl acetate. The extract was washed with water, dried over anhydrous sodium sulfate, and concentrated in vacuo. The resulting residue was subjected to column chromatography on silica gel and eluted with chloroform-methanol (20:1). The product was recrystallized from ethylacetate-hexane (1:2) to give 2,3,5-trimethyl-6-(5'-carboxy-1'-hydroxypentyl)-1,4-benzoquinone (formula I-3 wherein R=H₃C, n=4, in the free form) (0.128 part) as brown needles melting at 130°–131.5° C.

Elemental analysis, $C_{15}H_{20}O_5$— Calculated: C, 64.27; H, 10.24. Found: C, 64.03; H, 7.22.

EXAMPLE 45

A solution of 1-(2'-hydroxy-3',4',6'-trimethylphenyl)-1,6-hexanediol (formula III-3 wherein $R=H_3C$, $X=H$, $Y=OH$, $n=4$, in the free form) (5.43 parts) in acetic acid (150 volume parts) was stirred with 5% palladium on carbon (4.79 parts) under a stream of hydrogen gas at room temperature until the uptake of hydrogen ceased. The catalyst was filtered off and the filtrate was concentrated in vacuo. The resulting residue was subjected to column chromatography on silica gel and eluted with chloroform-methanol (100:1). From the 1st fraction, 6-(2'-hydroxy-3',4',6'-trimethylphenyl)hexanol (formula III-2, wherein $R=H_3C$, $X=H$, $Y=OH$, $n=4$, in the free form) (0.872 part) was obtained as colorless needles melting at 81°–82° C.

Elemental analysis, $C_{15}H_{24}O_2$— Calculated: C, 76.22; H, 10.24. Found: C, 76.08; H, 10.33.

From the 2nd fraction, the starting material (2.31 parts) was recovered.

EXAMPLE 46

To a solution of 6-(2'-hydroxy-3',4',6'-trimethylphenyl)hexanol (formula III-2, wherein $R=H_3C$, $X=H$, $Y=OH$, $n=4$, in the free form) (0.02 part) in 1% sodium hydroxide solution (25 parts) was added Fremy's salt (0.2 part) at room temperature with stirring. After being stirred for 1 hour, the mixture was cooled to 0° C., acidified with dilute hydrochloric acid, and extracted with ethyl acetate. The extract was washed with water, dried over anhydrous sodium sulfate, and concentrated in vacuo to give 2,3,5-trimethyl-6-(6'-hydroxyhexyl)-1,4-benzoquinone (formula IV-2 wherein $R=H_3C$, $n=4$, in the free form) (0.02 part) as yellow needles melting at 43°–45° C.

EXAMPLE 47

To a solution of 1-(2'-hydroxy-3',4',6'-trimethylphenyl)-1,6-hexanediol (formula III-3 wherein $R=H_3C$, $X=H$, $Y=OH$, $n=4$ in the free form) (0.32 part) in dimethyl formamide (20 volume parts) was added all at once a mixture of Fremy's salt (0.5 part) and potasium biphosphate(0.5 part) in water (50 volume parts). The mixture was stirred for 3 hours at room temperature. The reaction product was taken up with diethyl ether. The diethyl ether layer was washed with water and dried over anhydrous sodium sulfate. The residue upon removal of the solvent was subjected to chromatography on silica gel and eluted with ethyl acetate-diethyl ether (4:1) to give 2,3,5-trimethyl-6-(1',6'-dihydroxyhexyl)-1,4-benzoquinone (formula IV-3 wherein $R=H_3C$, $n=4$, in the free form) (0.26 part) as a yellow oil.

Infrared absorption spectrum $\nu_{max}^{film}$ cm$^{-1}$: 3400(OH), 1640 (quinone).

Nuclear magnetic resonance spectrum ($\tau$ in deuterochloroform): 8.55 ($CH_2$, broad), 8.00 (ring $CH_3$ singlet), 6.40(ring $CH_2$, triplet), 5.35(CH-O, broad).

Mass spectrum (m/e) $C_{15}H_{22}O_4$:$M^+$(266).

EXAMPLE 48

To a solution of 2,3,5-trimethyl-6-(1',6'-dihydroxyhexyl)-1,4-benzoquinone (formula IV-3 wherein $R=H_3C$, $n=4$, in the free form) (1.17 part) in anhydrous pyridine (15 volume parts) was added a solution of acetic anhydride (0.473 part) in pyridine (5 volume parts) dropwise under stirring at 5° C. The mixture was allowed to stand over night at room temperature. After removal of the solvents in vacuo, the residue was separated into two fractions by chromatography on silica gel and eluted with methylene chloride-diethyl ether (9:1). The 1st fraction afforded 2,3,5-trimethyl-6-(1',6'-diacetoxyhexyl)-1,4-benzoquinone (formula IV-3 wherein $R=H_3C$, $n=4$, in the form of diacetate at —$CH_2OH$ and

(0.265 part) as a yellow oil.

Infrared absorption spectrum $\nu_{max}^{film}$ cm$^{-1}$: 1740, 1370, 1250, 1040(OCOCH$_3$), 1640(quinone).

Nuclear magnetic resonance spectrum ($\tau$ in deuterochloroform): 8.50($CH_2$, broad), 7.99, 7.98, 7.95, 6.85 (ring $CH_3$, OCOCH$_3$), 5.96($CH_2$-O, triplet), 4.05(CH-O, triplet).

The 2nd fraction from the above mentioned chromtography afforded 2,3,5-trimethyl-6-(6'-acetoxy-1'-hydroxyhexyl)-1,4-benzoquinone (formula IV-3 wherein $R=H_3C$, $n=4$, in the form of acetate at —$CH_2OH$) (0.767 part) as a yellow oil.

Infrared absorption spectrum $\nu_{max}^{film}$ cm$^{-1}$: 3500(OH), 1740, 1250, 1040(OCOCH$_3$), 1640(quinone)

Nuclear magnetic resonance spectrum ($\tau$ in deuterochloroform): 8.50($CH_2$, broad), 7.99, 7.98, 7.97 (ring $CH_3$, OCOCH$_3$), 5.96($CH_2$-O, triplet), 4.05 (CH-O, triplet).

Mass spectrum (m/e) $C_{17}H_{24}O_5$:$M^+$(308).

EXAMPLE 49

A solution of 2,3,5-trimethyl-6-(6'-acetoxy-1'-hydroxyhexyl)-1,4-benzoquinone (formula IV-3 wherein $R=H_3C$, $n=4$, in the form of acetate at —$CH_2OH$) (0.74 part) in acetone (20 volume parts) was oxidized at 5° C. for 5 minutes with Jones reagent (0.6 volume part) prepared by dissolving chromic trioxide (26.72 parts) in concentrated sulfuric acid (23 volume parts) diluted with water to a volume of 100 volume parts. The resulting precipitate was decomposed with water, and the product was taken up with diethyl ether. The organic layer was washed with water and dried over anhydrous sodium sulfate. The residue upon removal of the solvent was subjected to column chromatography on silica gel and eluted with methylene chloride and the resulting product was crystallized from petroleum ether to give 2,3,5-trimethyl-6-(6'-acetoxy-1'-oxohexyl)-1,4-benzoquinone (formula IV-1 wherein $R=H_3C$, $n=4$, in the form of acetate) (0.638 part) as yellow crystals melting at 57° C.

Mass spectrum (m/e) $C_{17}H_{22}O_5$:$M^+$(306).

EXAMPLE 50

To a stirred mixture of 2,3,5-trimethyl-6-(6'-acetoxy-1'-oxohexyl)-1,4-benzoquinone (formula IV-1 wherein $R=H_3C$, $n=4$, in the form of acetate) (0.5 part), sodium hydrosulfite (1 part) and 30% aqueous methanol (20 volume parts) was added dropwise 2N aqueous sodium hydroxide (1.6 volume part) at 5° C. The mixture was allowed to stand for 3 hours at the same temperature. After removal of the methanol and acidification with phosphoric acid, the product was extracted with ethyl acetate. The organic layer was washed with water, dried over anhydrous sodium sulfate, and evaporated in vacuo. The residue was subjected to chromatography on silica gel and eluted with ethyl acetate to give 2,3,5-trimethyl-6-(6'-acetoxy-1'-oxohexyl)hydroquinone. (formula III-1 wherein R=$H_3$C, X=Y=OH, n=4, in the form of acetate) (0.075 part). Further elution with the same solvent gave 2,3,5-trimethyl-6-(6'-hydroxy-1'-oxohexyl)-hydroquinone. (formula III-1 wherein R=$H_3$C, X=Y=OH, n=4, in the free form) (0.265 part).

Infrared absorption spectrum $\nu_{max}^{film}$ cm$^{-1}$: 3450(OH), 1690 (quinone).

Nuclear magnetic resonance spectrum($\tau$ in deuterochloroform): 8.40($CH_2$, broad), 7.90(ring $CH_3$, singlet), 7.83(ring $CH_3$, singlet), 7.70(ring $CH_3$, singlet), 7.15(CO$CH_2$, broad), 6.40($CH_2$-O, broad).

EXAMPLE 51

A solution of 2,3,5-trimethyl-6-(6'-hydroxy-1'-oxohexyl)-hydroquinone (formula III-1 wherein R=$H_3$C, X=Y=OH, n=4, in the free form) (0.1 part) in diethyl ether (10 volume parts) was stirred with 3% aqueous ferric chloride solution at room temperature for 2 hours. The organic layer was separated and the aqueous layer was extracted with ethyl acetate. The combined organic layer and diethyl ether extract were washed with water, dried over anhydrous sodium sulfate, and evaporated in vacuo to dryness. The residue was subjected to chromatography on silica gel and eluted with diethyl ether to give 2,3,5-trimethyl-6-(6'-hydroxy-1'-oxohexyl)-1,4-benzoquinone (formula IV-1 wherein R=$H_3$C, n=4, in the free form) (0.088 part) as a yellow oil.

Infrared absorption spectrum $\nu_{max}^{film}$ cm$^{-1}$: 3450(OH), 1690(CO), 1640(quinone).

Nuclear magnetic resonance spectrum($\tau$ in deuterochloroform): 8.50($CH_2$, broad), 8.06(ring $CH_3$, singlet), 7.97(ring $CH_3$, singlet), 7.40(CO$CH_2$, triplet), 6.37($CH_2$-O, triplet).

Mass spectrum (m/e) $C_{15}H_{20}O_4$:M$^+$(264).

EXAMPLE 52

A solution of 2,3-dimethoxy-5-methyl-6-(3'-carboxypropyl)-1,4-benzoquinone (formula I-2 wherein R=$H_3$CO, n=2 in the free form (0.8 part) in ethanol (3 volume parts) saturated with dry hydrogen chloride was stirred at room temperature for 1 hour. The residue upon removal of the solvent was subjected to chromatography on silica gel and eluted with chloroform to give 2,3-dimethoxy-5-methyl-6-(3'-ethoxycarbonylpropyl)-1,4-benzoquinone (formula I-2 wherein R=$H_3$CO, n=2, in the form of ethyl ester) (0.88 part) as an orange oil.

Infrared absorption spectrum $\nu_{max}^{film}$ cm$^{-1}$: 1730(COO$C_2H_5$), 1660, 1640, 1610(quinone).

Nuclear magnetic resonance spectrum($\tau$ in deuterochloroform): 8.74($CH_3$, triplet), 8.56–8.00 ($CH_2$, multiplet), 7.96(ring $CH_3$, singlet), 7.65($CH_2$COO, triplet), 7.46(ring $CH_2$, triplet), 5.99(O$CH_3$, Singlet), 5.86(COO$CH_2$, quartet).

Elemental analysis, $C_{15}H_{20}O_6$— Calculated: C, 60.80; H, 6.80. Found: C, 61.26; H, 7.12.

EXAMPLE 53

To a well stirred solution of lithium aluminum hydride (0.5 part) in diethyl ether (5 volume parts) was added a solution of 2,3-dimethoxy-5-methyl-6-(3'-ethoxycarbonylpropyl)-1,4-benzoquinone (formula I-2 wherein R=$H_3$CO, n=2, in the form of ethyl ester) (0.78 part) in diethyl ether (10 volume parts) under cooling in ice-bath. After stirring at room temperature for 1 hour, the mixture was acidified with dilute hydrochloric acid. The diethyl ether layer was separated and the aqueous layer was extracted with diethyl ether. The combined diethyl ether and extract were washed with water, dried over anhydrous sodium sulfate. The diethyl ether was removed in vacuo to give 2,3-dimethoxy-5-methyl-6-(4'-hydroxybutyl)-hydroquinone (formula III-2 wherein R=$H_3$CO, n=2, in the free form). A solution of the above product in diethyl ether was shaken with 16% aqueous ferric chloride (10 volume parts). The diethyl ether layer was separated, washed with water and dried over anhydrous sodium sulfate. The residue upon removal of the solvent was subjected to chromatography on silica gel and eluted with chloroform to give 2,3-dimethoxy-5-methyl-6-(4'-hydroxybutyl)-1,4-benzoquinone (formula IV-2 wherein R=$H_3$CO, n=2, in the free form) (0.52 part) as an orange oil.

Infrared absorption spectrum $\nu_{max}^{film}$ cm$^{-1}$: 3400(OH), 1660, 1640, 1610(quinone).

Nuclear magnetic resonance spectrum ($\tau$ in deuterochloroform): 8.62–8.24($CH_2$, multiplet), 8.10(OH, singlet), 7.98(ring $CH_3$, singlet), 7.50(ring $CH_2$, triplet), 6.32($CH_2$O, triplet), 6.00(O$CH_3$, singlet).

Elemental analysis, $C_{13}H_{18}O_5$— Calculated: C, 61.40; H, 7.14. Found: C, 61.47; H, 7.32.

EXAMPLE 54

2,3-Dimethoxy-5-methyl-6-(9'-methoxycarbonylnonyl)-1,4-benzoquinone (formula I-2 wherein R=$H_3$CO, n=8, in the form of methyl ester) (1 part) was treated with lithium aluminum hydride in the same manner as Example 53 to give 2,3-dimethoxy-5-methyl-6-(10'-hydroxydecyl)-hydroquinone (formula III-2 wherein R=$H_3$CO, X=Y=OH, n=8, in the free form). The product was treated with ferric chloride in the same manner as Example 53 and then crystallized from ligroin. The procedure provided 2,3-dimethoxy-5-methyl-6-(10'-hydroxydecyl)-1,4-benzoquinone (formula IV-2 wherein R=$H_3$CO, n=8, in the free form) (0.65 part) as orange needles melting at 46°–50° C.

Elemental analysis, $C_{19}H_{30}O_5$— Calculated: C, 67.43; H, 8.94. Found: C, 67.41; H, 8.94.

EXAMPLE 55

To a cooled, well stirred solution of 2,3-dimethoxy-5-methyl-6-(10'-hydroxydecyl)-1,4-benzoquinone (formula IV-2 wherein R=$H_3$CO, n=8, in the free form) (0.3 part) in pyridine (1 volume part) was added acetic anhydride (0.1 volume part). After stirring at room temperature for 1 hour, the mixture was diluted with water, and the aqueous solution was extracted with diethyl ether. The extract was washed successively with water, dilute hydrochloric acid, water, saturated aqueous sodium hydrogen carbonate and water, and dried over anhydrous sodium sulfate. The residue upon removal of the solvent was crystallized from aqueous ethanol to give 2,3-dimethoxy-5-methyl-6-(10'-acetoxydecyl)-1,4-benzoquinone (formula IV-2 wherein R=$H_3$CO, n=8, in the form of acetate) (0.31 part) as orange needles melting at 38° C.

Elemental analysis, $C_{21}H_{32}O_6$— Calculated: C, 66.30; H, 8.48. Found: C, 66.12; H, 8.59.

EXAMPLE 56

A solution of 2,3,5-trimethyl-6-(2'-ethoxycarbonyle-thyl)-1,4-benzoquinone (formula I-2 wherein R=H$_3$C, n=1, in the form of ethyl ester) (0.39 part) in diethyl ether (50 volume parts) was treated with lithium aluminum hydride in the same manner as Example 53 to give 2,3,5-trimethyl-6-(3'-hydroxypropyl)-hydroquinone (formula III-2 wherein R=H$_3$C, X=Y=OH, n=1 in the free form). The product was treated with ferric chloride in the same manner as Example 53 and then subjected to column chromatography on silica gel and eluted with chloroform. The procedure provided 2,3,5-trimethyl-6-(3'-hydroxypropyl)-1,4-benzoquinone (formula IV-2 wherein R=H$_3$C, n=1, in the free form) (0.25 part) as a yellow oil.

Infrared absorption spectrum $\nu_{max}^{film}$ cm$^{-1}$: 3400(OH), 1640(quinone).

Nuclear magnetic resonance spectrum($\tau$ deuterochloroform): 8.50–8.06(CH$_2$, multiplet), 7.96(ring CH$_3$ singlet), 7.94(ring CH$_3$, singlet), 7.84(OH, broad), 7.40(ring CH$_2$, triplet), 6.40(CH$_2$O, triplet).

Mass spectrum (m/e) C$_{12}$H$_{16}$O$_3$:M$^+$(208).

EXAMPLE 57

To a well stirred solution of 2,3,5-trimethyl-6-(5'-carboxypentyl)-1,4-benzoquinone (formula I-2 wherein R=H$_3$C, n=4, in the free form) (0.21 part) in ethanol (10 volume parts) was added 3 drops of concentrated sulfuric acid under cooling in ice bath and kept standing for 12 hours. After addition of water, the reaction mixture was extracted with diethyl ether and the diethylether layer was washed with water and dried over anhydrous sodium sulfate. The residue upon removal of the solvent was subjected to chromatography on silica gel and eluted with chloroform to give 2,3,5-trimethyl-6-(5'-ethoxycarbonylpentyl)-1,4-benzoquinone (formula I-2 wherein R=H$_3$C, n=4, in the form of ethyl ester) (0.20 part) as an orange oil.

Infrared absorption spectrum $\sigma_{max}^{film}$ cm$^{-1}$: 1640 (quinone).

Nuclear magnetic resonance spectrum ($\tau$ in deuterochloroform): 8.76(CH$_3$, triplet), 8.80–8.30(CH$_2$, multiplet), 8.0 (ring CH$_3$, singlet), 8.00–7.30(ring CH$_2$, CH$_2$COO, multiplet), 5.88(COOCH$_2$, quartet).

Elemental analysis, C$_{17}$H$_{24}$O$_4$— Calculated: C, 69.83; H, 8.27. Found: C, 69.85; H, 8.36.

EXAMPLE 58

A solution of 2,3,5-trimethyl-6-(5'-ethoxycarbonylpentyl)-1,4-benzoquinone (formula I-2 wherein R=H$_3$C, n=4, in the form of ethylester) (0.1 part) in diethyl ether (10 volume parts) was treated with lithium aluminum hydride in the same manner as Example 53 to give 2,3,5-trimethyl-6-(6'-hydroxyhexyl)-hydroquinone (formula III-2 wherein R=H$_3$C, n=4, in the free form). The product was treated with ferric chloride in the same manner as Example 53 and then crystallized from diethyl ether. The procedure provided 2,3,5-trimethyl-6-(6'-hydroxyhexyl)-1,4-benzoquinone (formula IV-2, wherein R=H$_3$C, n=4 in the free form) as yellow needles melting at 43°–45° C.

Elemental analysis C$_{15}$H$_{22}$O$_3$— Calculated: C, 71.97; H, 8.86. Found: C, 72.33; H, 8.58.

EXAMPLE 59

Some examples of practical recipes in which the compounds of this invention are utilized for the physiologic host defense control are as follows:

A (Capsule)

(a)

| | |
|---|---|
| (1) 2,3-dimethoxy-5-methyl-6-(3'-ethoxycarbonylpropyl)-1,4-benzoquinone | 20 mg |
| (2) Corn oil | 150 mg |
| | 170 mg per capsule |

(1) is added to (2), and then warmed to about 40° C. to dissolve (1) in (2). The whole is filled into a gelatin capsule.

(b)

| | |
|---|---|
| (1) 2,3,5-trimethyl-6-(6'-hydroxyhexyl)-1,4-benzoquinone | 20 mg |
| (2) corn oil | 150 mg |
| | 170 mg per capsule |

Capsule is prepared in a similar manner as A-(a).

B (Tablet)

| | |
|---|---|
| (1) 2,3,5-trimethyl-6-(5'-carboxypentyl)-1,4-benzoquinone | 20 mg |
| (2) lactose | 35 mg |
| (3) corn starch | 150 mg |
| (4) microcrystalline cellulose | 30 mg |
| (5) magnesium stearate | 5 mg |
| | 240 mg per tablet |

(1),(2),(3), 2/3 quantity of (4) and half quantity of (5) are thoroughly mixed, and then the mixture is graulated. Remaining ⅓ quantity of (4) and half of (5) are added to the granules and compressed into tablets. Thus prepared tablets can further be coated with a suitable coating agent, e.g. sugar.

C (Injection)

(a)

| | |
|---|---|
| (1) 2,3-dimethoxy-5-methyl-6-(2'-carboxyethyl)-1,4 benzoquinone | 10 mg |
| (2) sodium bicarbonate | 3.3 mg |
| (3) sodium chloride | 0.018 mg |

(1) is dissolved in 1.5 ml of aqueous solution containing (2), to which (3) is added, then water is supplemented to make the whole volume 2.0 ml.

(b)

| | |
|---|---|
| (1) 2,3-dimethoxy-5-methyl-6-(5'-carboxy-1'-oxopentyl)-1,4-benzoquinone | 10 mg |
| (2) sodium bicarbonate | 2.7 mg |
| (3) sodium chloride | 0.018 mg |

An injection is prepared in a similar manner as C-(a).

(c)

| |
|---|
| (1) 2,3,5-trimethyl-6-(5'-carboxy-1'-hydroxy- |

| | |
|---|---|
| pentyl)-1,4-benzoquinone | 10 mg |
| (2) sodium bicarbonate | 3 mg |
| (3) sodium chloride | 0.018 mg |

An injection is prepared in a similar manner as C-(a).

What we claim is:

1. A compound selected from the group consisting of compounds of the formula

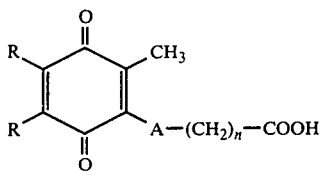

wherein R represents alkyl of 1–4 carbon atoms or alkoxy of 1–4 carbon atoms, A represents —CH₂—, —CO— or

and n represents an integer of from 1 to 8 when A is —CO— or

when both A is —CH₂— and R is alkoxy of 1–4 carbon atoms and an integer of from 4 to 8 when both A is —CH₂— and R is alkyl of 1–4 carbon atoms,
  alkyl esters of said compounds wherein the alkyl moiety of said alkyl esters has 1–4 carbon atoms,
  aryl esters of said compounds wherein the aryl moiety of said aryl esters has 6–7 carbon atoms, and
  aralkyl esters of said compounds wherein the aralkyl moiety of said aralkyl esters has 7–8 carbon atoms,
  said alkyl, aryl amd aralkyl moieties of said esters being unsubstituted or substituted by at least one of sulfo, carboxyl, formyl, hydroxyl and amino.

2. A compound as claimed in claim 1, wherein A is —CH₂—.

3. A compound as claimed in claim 1, wherein A is —CO—.

4. A compound as claimed in claim 1, wherein A is

5. A compound as claimed in claim 1, wherein R is alkyl of 1–4 carbon atoms.

6. A compound as claimed in claim 5, wherein n is 4 or 5.

7. A compound as claimed in claim 5, wherein R is methyl.

8. A compound as claimed in claim 1, wherein R is alkoxy of 1–4 carbon atoms.

9. A compound as claimed in claim 8, wherein R is methoxy.

10. A compound as claimed in claim 1, wherein the compound is in the form of an alkyl ester in which the alkyl moiety of said alkyl ester has 1–4 carbon atoms, said alkyl moiety of said ester being unsubstituted or substituted by at least one of sulfo, carboxyl, formyl, hydroxyl and amino.

11. A compound as claimed in claim 1, wherein the compound is in the form of an aryl ester in which the aryl moiety of said aryl ester has 6–7 carbon atoms, said aryl moiety of said ester being unsubstituted or substituted by at least one of sulfo, carboxyl, formyl, hydroxyl and amino.

12. A compound as claimed in claim 1, wherein the compound is in the form of an aralkyl ester in which the aralkyl moiety of said aralkyl ester has 7–8 carbon atoms, said aralkyl moiety of said ester being unsubstituted or substituted by at least one of sulfo, carboxyl, formyl, hydroxyl and amino.

13. The compound as claimed in claim 1, wherein the compound is 2,3,5-trimethyl-6-[5′-(o-carboxyphenyloxycarbonyl)pentyl]-1,4-benzoquinone.

14. The compound as claimed in claim 1, wherein the compound is 2,3,5-trimethyl-6-(5′-carboxypentyl)-1,4-benzoquinone.

15. The compound as claimed in claim 1, wherein the compound is 2,3,5-trimethyl-6-(9′-carboxynonyl)-1,4-benzoquinone.

16. The compound as claimed in claim 1, wherein the compound is 2,3-dimethoxy-5-methyl-6-(2′-carboxyethyl)-1,4-benzoquinone.

17. The compound as claimed in claim 1, wherein the compound is 2,3-dimethoxy-5-methyl-6-(9′-carboxynonyl)-1,4-benzoquinone.

18. The compound as claimed in claim 1, wherein the compound is 2,3,5-trimethyl-6-(5′-ethoxycarbonylpentyl)-1,4-benzoquinone.

19. The compound as claimed in claim 1, wherein the compound is 2,3,5-trimethyl-6-(5′-carboxy-1′-oxopentyl)-1,4-benzoquinone.

20. The compound as claimed in claim 1, wherein the compound is 2,3-dimethoxy-5-methyl-6-(5′-carboxy-1′-oxopentyl)-1,4-benzoquinone.

21. The compound as claimed in claim 1, wherein the compound is 2,3,5-trimethyl-6-(5′-carboxy-1′-hydroxypentyl)-1,4-benzoquinone.

* * * * *

UNITED STATES PATENT AND TRADEMARK OFFICE
CERTIFICATE OF CORRECTION

PATENT NO. : 4,139,545

DATED : Februsry 13, 1979

INVENTOR(S) : Hiroshi Morimoto et al.

It is certified that error appears in the above—identified patent and that said Letters Patent is hereby corrected as shown below:

Claim 1, line 11 (the line beginning with "when both"), insert -- or -- at the beginning of the line.

Claim 1, line 3 from the bottom, change "amd" to -- and --.

Signed and Sealed this

Twenty-sixth Day of May 1981

[SEAL]

Attest:

RENE D. TEGTMEYER

Attesting Officer     Acting Commissioner of Patents and Trademarks